(12) United States Patent
Haertle et al.

(10) Patent No.: US 9,689,014 B2
(45) Date of Patent: Jun. 27, 2017

(54) USE OF LYSOZYME AS A TAG

(71) Applicant: MorphoSys AG, Martinsried/Planegg (DE)

(72) Inventors: Stefan Haertle, Jensenwang (DE); Sebastian Jaeger, Graefelfing (DE); Daniela Daubert, Olching (DE)

(73) Assignee: MORPHOSYS AG, Planegg (DE)

(*) Notice: Subject to any disclaimer, the term of this patent is extended or adjusted under 35 U.S.C. 154(b) by 35 days.

(21) Appl. No.: 14/368,513

(22) PCT Filed: Jan. 23, 2013

(86) PCT No.: PCT/EP2013/051181
§ 371 (c)(1),
(2) Date: Jun. 25, 2014

(87) PCT Pub. No.: WO2013/110627
PCT Pub. Date: Aug. 1, 2013

(65) Prior Publication Data
US 2014/0349343 A1 Nov. 27, 2014

Related U.S. Application Data

(60) Provisional application No. 61/589,408, filed on Jan. 23, 2012.

(30) Foreign Application Priority Data

Jan. 23, 2012 (EP) ..................... 12152095

(51) Int. Cl.
| | | |
|---|---|---|
| C12N 15/09 | (2006.01) | |
| C12P 21/00 | (2006.01) | |
| C07K 1/22 | (2006.01) | |
| C12N 15/62 | (2006.01) | |
| C12P 21/02 | (2006.01) | |

(52) U.S. Cl.
CPC ............... *C12P 21/00* (2013.01); *C07K 1/22* (2013.01); *C12N 15/62* (2013.01); *C12P 21/02* (2013.01); *C07K 2319/00* (2013.01); *C07K 2319/35* (2013.01)

(58) Field of Classification Search
CPC .................................................. C12N 15/09
USPC ............................... 435/183, 69.1
See application file for complete search history.

(56) References Cited

U.S. PATENT DOCUMENTS

| | | | |
|---|---|---|---|
| 4,355,022 A | 10/1982 | Rabussay | |
| 7,045,677 B2 | 5/2006 | Cottingham | |
| 7,428,273 B2 | 9/2008 | Foster | |
| 7,790,850 B2 * | 9/2010 | Kobilka | ........... C07K 14/70571 |
| | | | 435/69.7 |

FOREIGN PATENT DOCUMENTS

| | | |
|---|---|---|
| EP | 0332323 | 9/1989 |
| EP | 0425016 | 12/1995 |
| WO | 0021381 | 4/2000 |
| WO | 0100855 | 1/2001 |
| WO | 03057174 | 7/2003 |
| WO | 2004026334 | 1/2004 |
| WO | 2004017988 | 3/2004 |
| WO | 2005080559 | 9/2005 |
| WO | 2008124764 | 10/2008 |
| WO | 2009051769 | 4/2009 |

OTHER PUBLICATIONS

Smith-Gill, et al: "A three-dimensional model of an anti-lysozyme antibody", Journal of Molecular Biology, Academic Press, vol. 194, No. 4, Apr. 20, 1987.
PCT/EP2013/05181; International Search Report dated Mar. 12, 2013.
EP12152095.1; European Search Report dated Jun. 11, 2012.
Sumo TM Poster: "Champion pET Expression with SUMO tag enables high-level soluble expression and purification of recombinant proteins and peptides with native N-termini in *E. coli*.".
Invitrogen; Champion pET SUMO Protein, Expression System "For high-level expression and enhanced solubility of recombinant proteins in *E. coil* and cleavage of native protein" Catalog No. K300-01, Rev. Date: Jun. 18, 2010, Manual part No. 25/0709.
Hughey and Johnson (1987) Appl. Environ Microbiol 53:2165; 1987.
Streuli and Bissell (1990) The Journal of Cell Biology, vol. 110, Apr. 1990; 1405-1415.
Furth et al. (1991), 19 Nucleic Acids Res. 6205.
Whitelaw et al. (1991), Transgenic Res. 3.

* cited by examiner

*Primary Examiner* — Maryam Monshipouri
(74) *Attorney, Agent, or Firm* — Licata & Tyrrell P.C.

(57) ABSTRACT

The present disclosure provides a method to express and purify polypeptides and proteins. In the present disclosure the use of lysozyme as a fusion partner is disclosed. Furthermore, purification methods to isolate lysozyme-tagged polypeptides and proteins via lysozyme-specific antibodies are described. More specifically, the present disclosure provides a method to express and purify monomeric polypeptides and proteins by using lysozyme as a tag.

9 Claims, 4 Drawing Sheets

Figure 2A

```
   1    GATCTCCCGA TCCCCTATGG TGCACTCTCA GTACAATCTG CTCTGATGCC
  51    GCATAGTTAA GCCAGTATCT GCTCCCTGCT TGTGTGTTGG AGGTCGCTGA
 101    GTAGTGCGCG AGCAAAATTT AAGCTACAAC AAGGCAAGGC TTGACCGACA
 151    TTTGCATGAA GAATCTGCTT AGGGTTAGGC GTTTTGCGCT GCTTCGCGAT
 201    GTACGGGCCA GATATACGCG TTGACATTGA TTATTGACTA GTTATTAATA
 251    GTAATCAATT ACGGGGTCAT TAGTTCATAG CCCATATATG GAGTTCCGCG
 301    TTACATAACT TACGGTAAAT GGCCCGCCTG GCTGACCGCC CAACGACCCC
 351    CGCCCATTGA CGTCAATAAT GACGTATGTT CCCATAGTAA CGCCAATAGG
 401    GACTTTCCAT TGACGTCAAT GGGTGGAGTA TTTACGGTAA ACTGCCCACT
 451    TGGCAGTACA TCAAGTGTAT CATATGCCAA GTACGCCCCC TATTGACGTC
 501    AATGACGGTA AATGGCCCGC CTGGCATTAT GCCCAGTACA TGACCTTATG
 551    GGACTTTCCT ACTTGGCAGT ACATCTACGT ATTAGTCATC GCTATTACCA
 601    TGGTGATGCG GTTTTGGCAG TACATCAATG GGCGTGGATA GCGGTTTGAC
 651    TCACGGGGAT TTCCAAGTCT CCACCCCATT GACGTCAATG GGAGTTTGTT
 701    TTGGCACCAA AATCAACGGG ACTTTCCAAA ATGTCGTAAC AACTCCGCCC
 751    CATTGACGCA AATGGGCGGT AGGCGTGTAC GGTGGGAGGT CTATATAAGC
 801    AGAGCTCTCT GGCTAACTAG AGAACCCACT GCTTACTGGC TTATCGAAAT
 851    TAATACGACT CACTATAGGG AGACCCAAGC TGGCTAGCAA GCTTCTAGCG
 901    CCACCATGGT GTTGCAGACC CAGGTCTTCA TTTCTCTGTT GCTCTGGATC
 951    TCTGGTGCCT ACGGGGATGG TACCGGGAAA ATGATGGATA TCATCGAGGG
1001    CCGGATGGAC AAGGTGTTCG GCAGATGCGA GCTGGCCGCT GCCATGAAGC
1051    GGCACGGCCT GGACAACTAC CGGGGCTACA GCCTGGGCAA CTGGGTCTGC
1101    GCCGCCAAGT TCGAGAGCAA CTTCAATACT CAGGCCACCA ACCGGAACAC
1151    CGACGGCAGC ACCGACTACG GCATCCTGCA GATCAACAGC CGGTGGTGGT
1201    GCAACGACGG CAGGACCCCC GGCAGCCGGA ACCTGTGCAA CATCCCTTGC
1251    AGCGCCCTGC TGTCCAGCGA CATCACCGCC AGCGTGAACT GCGCCAAGAA
1301    AATCGTGTCC GACGGCAACG GCATGAACGC CTGGGTGGCC TGGCGGAACC
1351    GGTGCAAGGG CACAGACGTG CAGGCCTGGA TCAGAGGCTG CAGACTGGTT
1401    AACTCTAGAG GTCTGAACGA CATCTTCGAG GCTCAGAAAA TCGAATGGCA
1451    CGAATAATGA GAATTCTCTA GATAATGAGT TTAAACGGGT GGCATCCCTG
1501    TGACCCCTCC CCAGTGCCTC TCCTGGCCCT GGAAGTTGCC ACTCCAGTGC
1551    CCACCAGCCT TGTCCTAATA AAATTAAGTT GCATCATTTT GTCTGACTAG
1601    GTGTCCTTCT ATAATATTAT GGGGTGGAGG GGGGTGGTAT GGAGCAAGGG
1651    GCAAGTTGGG AAGACAACCT GTAGGGCCTG CGGGGTCTAT TGGGAACCAA
1701    GCTGGAGTGC AGTGGCACAA TCTTGGCTCA CTGCAATCTC CGCCTCCTGG
1751    GTTCAAGCGA TTCTCCTGCC TCAGCCTCCC GAGTTGTTGG GATTCCAGGC
1801    ATGCATGACC AGGCTCACCT AATTTTGTT TTTTGGTAG AGACGGGGTT
1851    TCACCATATT GGCCAGGCTG GTCTCCAACT CCTAATCTCA GGTGATCTAC
1901    CCACCTTGGC CTCCCAAATT GCTGGGATTA CAGGCGTGAA CCACTGCTCC
1951    CTTCCCTGTC CTTCTGATTT TAAAATAACT ATACCAGCAG GAGGACGTCC
2001    AGACACAGCA TAGGCTACCT GGCCATGCCC AACCGGTGGG ACATTTGAGT
2051    TGCTTGCTTG GCACTGTCCT CTCATGCGTT GGGTCCACTC AGTAGATGCC
2101    TGTTGAATTG GGTACGCGGC ATCGATTCCA CGCGCCCTGT AGCGGCGCAT
2151    TAAGCGCGGC GGGTGTGGTG GTTACGCGCA GCGTGACCGC TACACTTGCC
2201    AGCGCCCTAG CGCCCGCTCC TTTCGCTTTC TTCCCTTCCT TTCTCGCCAC
2251    GTTCGCCGGC TTTCCCCGTC AAGCTCTAAA TCGGGGGCTC CCTTTAGGGT
2301    TCCGATTTAG TGCTTTACGG CACCTCGACC CCAAAAAACT TGATTAGGGT
2351    GATGGTTCAC GTAGTGGGCC ATCGCCCTGA TAGACGGTTT TTCGCCCTTT
2401    GACGTTGGAG TCCACGTTCT TTAATAGTGG ACTCTTGTTC CAAACTGGAA
2451    CAACACTCAA CCCTATCTCG GTCTATTCTT TTGATTTATA AGGGATTTTG
2501    CCGATTTCGG CCTATTGGTT AAAAAATGAG CTGATTTAAC AAAAATTTAA
```

Figure 2B

```
2551  CGCGAATTAA TTCTGTGGAA TGTGTGTCAG TTAGGGTGTG GAAAGTCCCC
2601  AGGCTCCCCA GCAGGCAGAA GTATGCAAAG CATGCATCTC AATTAGTCAG
2651  CAACCAGGTG TGGAAAGTCC CCAGGCTCCC CAGCAGGCAG AAGTATGCAA
2701  AGCATGCATC TCAATTAGTC AGCAACCATA GTCCCGCCCC TAACTCCGCC
2751  CATCCCGCCC CTAACTCCGC CCAGTTCCGC CCATTCTCCG CCCCATGGCT
2801  GACTAATTTT TTTTATTTAT GCAGAGGCCG AGGCCGCCTC TGCCTCTGAG
2851  CTATTCCAGA AGTAGTGAGG AGGCTTTTTT GGAGGCCTAG GCTTTTGCAA
2901  AAAGCTCCCG GGAGCTTGTA TATCCATTTT CGGATCTGAT CAAGAGACAG
2951  GATGAGGATC GTTTCGCATG ATTGAACAAG ATGGATTGCA CGCAGGTTCT
3001  CCGGCCGCTT GGGTGGAGAG GCTATTCGGC TATGACTGGG CACAACAGAC
3051  AATCGGCTGC TCTGATGCCG CCGTGTTCCG GCTGTCAGCG CAGGGGCGCC
3101  CGGTTCTTTT TGTCAAGACC GACCTGTCCG GTGCCCTGAA TGAACTGCAG
3151  GACGAGGCAG CGCGGCTATC GTGGCTGGCC ACGACGGGCG TTCCTTGCGC
3201  AGCTGTGCTC GACGTTGTCA CTGAAGCGGG AAGGGACTGG CTGCTATTGG
3251  GCGAAGTGCC GGGGCAGGAT CTCCTGTCAT CTCACCTTGC TCCTGCCGAG
3301  AAAGTATCCA TCATGGCTGA TGCAATGCGG CGGCTGCATA CGCTTGATCC
3351  GGCTACCTGC CCATTCGACC ACCAAGCGAA ACATCGCATC GAGCGAGCAC
3401  GTACTCGGAT GGAAGCCGGT CTTGTCGATC AGGATGATCT GGACGAAGAG
3451  CATCAGGGGC TCGCGCCAGC CGAACTGTTC GCCAGGCTCA AGGCGCGCAT
3501  GCCCGACGGC GAGGATCTCG TCGTGACCCA TGGCGATGCC TGCTTGCCGA
3551  ATATCATGGT GGAAAATGGC CGCTTTTCTG GATTCATCGA CTGTGGCCGG
3601  CTGGGTGTGG CGGACCGCTA TCAGGACATA GCGTTGGCTA CCCGTGATAT
3651  TGCTGAAGAG CTTGGCGGCG AATGGGCTGA CCGCTTCCTC GTGCTTTACG
3701  GTATCGCCGC TCCCGATTCG CAGCGCATCG CCTTCTATCG CCTTCTTGAC
3751  GAGTTCTTCT GAGCGGGACT CTGGGGTTCG AAATGACCGA CCAAGCGACG
3801  CCCAACCTGC CATCACGAGA TTTCGATTCC ACCGCCGCCT TCTATGAAAG
3851  GTTGGGCTTC GGAATCGTTT TCCGGACGC CGGCTGGATG ATCCTCCAGC
3901  GCGGGGATCT CATGCTGGAG TTCTTCGCCC ACCCCAACTT GTTTATTGCA
3951  GCTTATAATG GTTACAAATA AAGCAATAGC ATCACAAATT TCACAAATAA
4001  AGCATTTTTT TCACTGCATT CTAGTTGTGG TTTGTCCAAA CTCATCAATG
4051  TATCTTATCA TGTCTGTATA CCGTCGACCT CTAGCTAGAG CTTGGCGTAA
4101  TCATGGTCAT AGCTGTTTCC TGTGTGAAAT TGTTATCCGC TCACAATTCC
4151  ACACAACATA CGAGCCGGAA GCATAAAGTG TAAAGCCTGG GGTGCCTAAT
4201  GAGTGAGCTA ACTCACATTA ATTGCGTTGC GCTCACTGCC CGCTTTCCAG
4251  TCGGGAAACC TGTCGTGCCA GCTGCATTAA TGAATCGGCC AACGCGCGGG
4301  GAGAGGCGGT TTGCGTATTG GGCGCTCTTC CGCTTCCTCG CTCACTGACT
4351  CGCTGCGCTC GGTCGTTCGG CTGCGGCGAG CGGTATCAGC TCACTCAAAG
4401  GCGGTAATAC GGTTATCCAC AGAATCAGGG GATAACGCAG GAAAGAACAT
4451  GTGAGCAAAA GGCCAGCAAA AGGCCAGGAA CCGTAAAAAG GCCGCGTTGC
4501  TGGCGTTTTT CCATAGGCTC CGCCCCCCTG ACGAGCATCA CAAAAATCGA
4551  CGCTCAAGTC AGAGGTGGCG AAACCCGACA GGACTATAAA GATACCAGGC
4601  GTTTCCCCCT GGAAGCTCCC TCGTGCGCTC TCCTGTTCCG ACCCTGCCGC
4651  TTACCGGATA CCTGTCCGCC TTTCTCCCTT CGGGAAGCGT GGCGCTTTCT
4701  CATAGCTCAC GCTGTAGGTA TCTCAGTTCG GTGTAGGTCG TTCGCTCCAA
4751  GCTGGGCTGT GTGCACGAAC CCCCCGTTCA GCCCGACCGC TGCGCCTTAT
4801  CCGGTAACTA TCGTCTTGAG TCCAACCCGG TAAGACACGA CTTATCGCCA
4851  CTGGCAGCAG CCACTGGTAA CAGGATTAGC AGAGCGAGGT ATGTAGGCGG
4901  TGCTACAGAG TTCTTGAAGT GGTGGCCTAA CTACGGCTAC ACTAGAAGAA
4951  CAGTATTTGG TATCTGCGCT CTGCTGAAGC CAGTTACCTT CGGAAAAAGA
5001  GTTGGTAGCT CTTGATCCGG CAAACAAACC ACCGCTGGTA GCGGTGGTTT
5051  TTTTGTTTGC AAGCAGCAGA TTACGCGCAG AAAAAAAGGA TCTCAAGAAG
```

Figure 2C

```
5101  ATCCTTTGAT CTTTTCTACG GGGTCTGACG CTCAGTGGAA CGAAAACTCA
5151  CGTTAAGGGA TTTTGGTCAT GAGATTATCA AAAAGGATCT TCACCTAGAT
5201  CCTTTTAAAT TAAAAATGAA GTTTTAAATC AATCTAAAGT ATATATGAGT
5251  AAACTTGGTC TGACAGTTAC CAATGCTTAA TCAGTGAGGC ACCTATCTCA
5301  GCGATCTGTC TATTTCGTTC ATCCATAGTT GCCTGACTCC CCGTCGTGTA
5351  GATAACTACG ATACGGGAGG GCTTACCATC TGGCCCCAGT GCTGCAATGA
5401  TACCGCGAGA CCCACGCTCA CCGGCTCCAG ATTTATCAGC AATAAACCAG
5451  CCAGCCGGAA GGGCCGAGCG CAGAAGTGGT CCTGCAACTT TATCCGCCTC
5501  CATCCAGTCT ATTAATTGTT GCCGGGAAGC TAGAGTAAGT AGTTCGCCAG
5551  TTAATAGTTT GCGCAACGTT GTTGCCATTG CTACAGGCAT CGTGGTGTCA
5601  CGCTCGTCGT TTGGTATGGC TTCATTCAGC TCCGGTTCCC AACGATCAAG
5651  GCGAGTTACA TGATCCCCCA TGTTGTGCAA AAAAGCGGTT AGCTCCTTCG
5701  GTCCTCCGAT CGTTGTCAGA AGTAAGTTGG CCGCAGTGTT ATCACTCATG
5751  GTTATGGCAG CACTGCATAA TTCTCTTACT GTCATGCCAT CCGTAAGATG
5801  CTTTTCTGTG ACTGGTGAGT ACTCAACCAA GTCATTCTGA GAATAGTGTA
5851  TGCGGCGACC GAGTTGCTCT TGCCCGGCGT CAATACGGGA TAATACCGCG
5901  CCACATAGCA GAACTTTAAA AGTGCTCATC ATTGGAAAAC GTTCTTCGGG
5951  GCGAAAACTC TCAAGGATCT TACCGCTGTT GAGATCCAGT TCGATGTAAC
6001  CCACTCGTGC ACCCAACTGA TCTTCAGCAT CTTTTACTTT CACCAGCGTT
6051  TCTGGGTGAG CAAAAACAGG AAGGCAAAAT GCCGCAAAAA AGGGAATAAG
6101  GGCGACACGG AAATGTTGAA TACTCATACT CTTCCTTTTT CAATATTATT
6151  GAAGCATTTA TCAGGGTTAT TGTCTCATGA GCGGATACAT ATTTGAATGT
6201  ATTTAGAAAA ATAAACAAAT AGGGGTTCCG CGCACATTTC CCCGAAAAGT
6251  GCCACCTGAC GTCGACGGAT CGGGA
```

USE OF LYSOZYME AS A TAG

CROSS REFERENCE

This application claims the benefit of U.S. provisional application Ser. No. 61/589,408 filed Jan. 23, 2012, which is incorporated by reference in its entireties.

BACKGROUND OF THE INVENTION

Expression and purification of recombinant polypeptides and proteins is a routine process within biotechnological research. In general the process of purification comprises the expression of a desired polypeptide in prokaryotic or eukaryotic cells followed by the separation from other non-proteinacious and proteinacious particles of the host cell. Thereby various types of chromatography are used to purify the desired molecule e.g. by size, charge or hydrophobicity.

One further specific strategy is to use a tag which is fused to the polypeptide of interest. Specific tags can be used to support the folding, solubility, stability and expression of the polypeptide of interest while other tags are mainly used for purification. Thereby the desired polypeptide is expressed as a fusion construct in prokaryotic or eukaryotic cells and can be purified via the fused tag which is detected by a specific antigen binding moiety. This kind of purification strategy is called affinity chromatography.

One purification-tag used in the scientific community is e.g. the His-tag. Thereby the polypeptides which are fused with a His-tag can be separated by using e.g. a purification column with immobilized nickel or cobalt ions that have strong affinity to the His-tag. The protein is then released from the column in an elution process involving imidazole which competes with the His-tags for nickel or cobalt binding. Further examples are the Flag-tag and the Strep-tag which are both fused to the polypeptide of interest and serve as an antigen for respective tag-specific antigen binding moieties like e.g. antibodies or Streptactin, respectively. These binding moieties (e.g. antibodies, streptactin or metal ions) which are used for purification (e.g. via the Flag-tag, Strep-tag or His-tag, respectively) can e.g. be immobilized on a solid substrate (e.g. membranes, beads). Those solid substrates coupled with specific binding moieties for defined tags can be used to easily capture the tagged polypeptide from complex samples as lysates or conditioned media. However, the Flag-, Strep- and His-tags which are short peptides are sometimes not accessible within the 3-dimensional structure of specific polypeptides or proteins and thus not suitable for purification. Additionally, purification from mammalian cell culture supernatants via the Strep-tag is impaired due to the high biotin concentrations of most media.

Certain larger globular tags can support the folding, solubility and expression of difficult-to-express polypeptides as proteins. Most available gene-fusion-technologies were developed for expression in *E. coli* and purification from crude lysates. Examples of those fusion proteins are MBP (Maltose binding protein), GST (Glutathione-S-Transferase) and SUMO (small ubiquitin modifying protein; see for example WO 03/057174).

The SUMO-tag has originally been designed for prokaryotic expression (e.g. SUMOpro™ Expression Kit, www.lifesensors.com), and was then further developed for mammalian expression (SUMOstar™ Expression Kit, www.lifesensors.com). SUMO functions both as a chaperon and as an initiator of protein folding to improve the solubility and level of expression of the protein of interest. By using a desumoylase, the SUMO tag, fused to the N-terminus of the protein of interest, can be removed resulting in the production of native N-terminus of the protein. Fusion of SUMO tag to the C-terminus of the protein of interest does not allow the removal of the fusion tag. Purification of the target protein fused to SUMO tag does not utilize the SUMO tag but requires the application of a purification tag such as His-tag.

An alternative for mammalian expression is the usage of the Fc-tag which comprises the hinge-region, the CH2 and CH3 domain of the human IgG1. The Fc-tag is used to support expression, folding and secretion of specific polypeptides and in parallel is also used as a tag for its purification. While the His- and the Flag-tag are short peptides with low molecular weight and well suited for the expression of soluble polypeptides and proteins, the Fc-tag is a polypeptide of more than 200 amino acids and supports the expression of specific hydrophobic less-soluble proteins. However, the relatively large Fc-portion forms disulfide-bridged aggregates, resulting in dimeric or multimeric forms of the isolated and purified protein of interest.

Other common alternatives are the GST (glutathione S-transferase) and MBP (maltose binding protein), which bind to glutathione and maltose, respectively. Both tags are of high molecular weight (>25 kDa) and significantly increase the solubility and stability of a polypeptide or protein of interest. However, both gene-fusion systems cannot be used for protein purification of secreted proteins from conditioned mammalian cell culture supernatants as ingredients of the media prevent binding of the fusion tag to its binding partner, i.e. glutathione or maltose. Additionally, both fusion tags have a tendency to aggregate in mammalian expression systems and also tend to form inclusion bodies.

Hence, while e.g. the Fc-Tag, is not suited for the expression and purification of monomeric polypeptides and proteins, all other available tags have specific assets and drawbacks and are not suited for the expression and/or purification of certain specific polypeptides or proteins. Taken together, the quality of expression and purification not only depends on the nature of the polypeptide or protein of interest but also on the respective tag that is used. Thus the combination of a specific tag and a specific polypeptide or protein of interest is crucial for best results but hardly predictable. Consequently, there is an inexhaustible need for novel and convenient tags that enable expression and purification or improve quality of specific challenging recombinant polypeptides and proteins. The methods disclosed in the present application provide an efficient way to express and purify polypeptide or protein by using lysozyme as a tag.

SUMMARY OF THE INVENTION

The present disclosure provides a method to express and purify monomeric polypeptides and proteins. The present disclosure enables the purification of polypeptides and proteins which cannot be expressed and purified by using other tags known in the art. In the present disclosure the use of lysozyme as a fusion partner is disclosed. Furthermore, purification methods to isolate lysozyme-tagged polypeptides and proteins via lysozyme-specific antibodies are described. The use of lysozyme as a tag turned out to enable the expression of specific monomeric polypeptides and proteins or improved expression rates of polypeptides and proteins in comparison to other tags that are state of the art. Improper folding, low solubility and expression, loss of activity as well as aggregation of the isolated polypeptides, leading to the formation of unwanted and undesirable multimeric proteins can be circumvented by using lysozyme as a fusion partner. Moreover, another advantage of using lysozyme is its antibacterial activity that allows the reduction or eschewal of antibiotics which usually are required for the process of cell culturing and protein expression under sterile conditions.

Lysozyme (EC 3.2.1.17) also known as muramidase or N-acetylmuramide glycanhydrolase has a molecular weight of approximately 14.6 kDa and catalyzes hydrolysis of 1,4-beta-linkages between N-acetylmuramic acid and N-acetyl-D-glucosamine residues in a peptidoglycan and between N-acetyl-D-glucosamine residues in chitodextrins.

Lysozyme is typically produced as a defensive mechanism against bacteria by many organisms, such as viruses, plants, insects, birds, reptiles and mammals. The enzyme causes the hydrolysis of bacterial cell walls by cleaving the glycosidic bonds of peptidoglycan, an important structural molecule in bacteria. After having their cell walls weakened by lysozyme action, bacterial cells lyse as a result from osmotic pressure.

Lysozyme has been classified into five different glycoside hydrolase (GH) families (Cazy, www.cazy.org): hen egg-white lysozyme (GH22), goose egg-white lysozyme (GH23), bacteriophage T4 lysozyme (GH24), *Sphingomonas flagellar* protein (GH73) and Chalaropsis lysozymes (GH25). The lysozyme family GH25 has been found to be structurally unrelated to the other Lysozyme families.

Use of lysozyme has been suggested in animal feed (see for example WO 00/21381 and WO 04/026334), in cheese production (see for example WO 05/080559), for food preservation (Hughey and Johnson (1987) Appl Environ Microbiol 53:2165), as detergents (see for example U.S. Ser. No. 07/428,273 and EP 0425016), in oral care (see for example U.S. Ser. No. 06/279,536, WO04/017988 and WO08/124764), in cosmetology and dermatology, contraception, urology, and gynecology (see for example WO 08/124764). Hen egg-white lysozyme is a commercially available lysozyme product. Lysozymes isolated from microbial but also mammalian sources are also known. However, there is no public report of recombinant lysozyme expression in mammalian cell cultures or the expression of peptides or proteins fused to lysozyme in cell culture.

U.S. Ser. No. 10/024,597 and WO 01/00855 disclose the expression of small peptides fused to lysozyme in milk of transgenic animals. Because lysozyme is a naturally expressed milk protein the lysozyme-fused peptides were expressed and the basic lysozyme fusion peptides could be purified from the predominantly acidic proteins in milk. However, cells from mammary glands were described as being not able to produce milk proteins, such as lysozyme, in cell culture (Streuli and Bissell (1990) The Journal of Cell Biology, Volume 110, April 1990 1405-1415). Furthermore, protein expression of milk proteins in transgenic animals is not predictable for cell culture expression and respective findings can not be transferred to cell culture systems (see e.g. Furth et al., (1991), 19 Nucleic Acids Res. 6205 and Whitelaw et al., (1991); 1 Transgenic Res. 3).

In another application, Kobilka et al. used lysozyme as a stabilizer for G-protein coupled receptors (GPCRs) to enable the crystallization of GPCRs. Thereby, T4 lysozyme is inserted into one of the intracellular loops of the respective GPCR expressed in insect cells. (see WO 09/051769).

The present disclosure provides a method for the production and purification of isolated proteins, peptides and/or amino acids in a host cell, wherein said proteins, peptides and/or amino acids are fused to lysozyme, said method comprising
  (a) culturing said host cell under conditions that allow the expression of a gene encoding a protein of interest, and,
  (b) isolating said proteins, peptides or amino acids.

The present disclosure also provides host cells and vectors to be used in the methods disclosed herein. The present disclosure also provides reaction vessels, such as fermenters, for use in the methods of the present invention. The present invention also provides a kit, comprising
  (a) a vector according to the present invention,
  (b) an antibody specific for lysozyme, and
  (c) optionally, instructions to use the said vector and antibody in accordance with the methods described herein.

DESCRIPTION OF THE FIGURES

FIG. 2A-C: Nucleotide sequence encoding entire pMax expression construct (SEQ ID NO: 15) comprising chicken lysozyme (underlined).

DETAILED DESCRIPTION OF THE INVENTION

Figure 1:
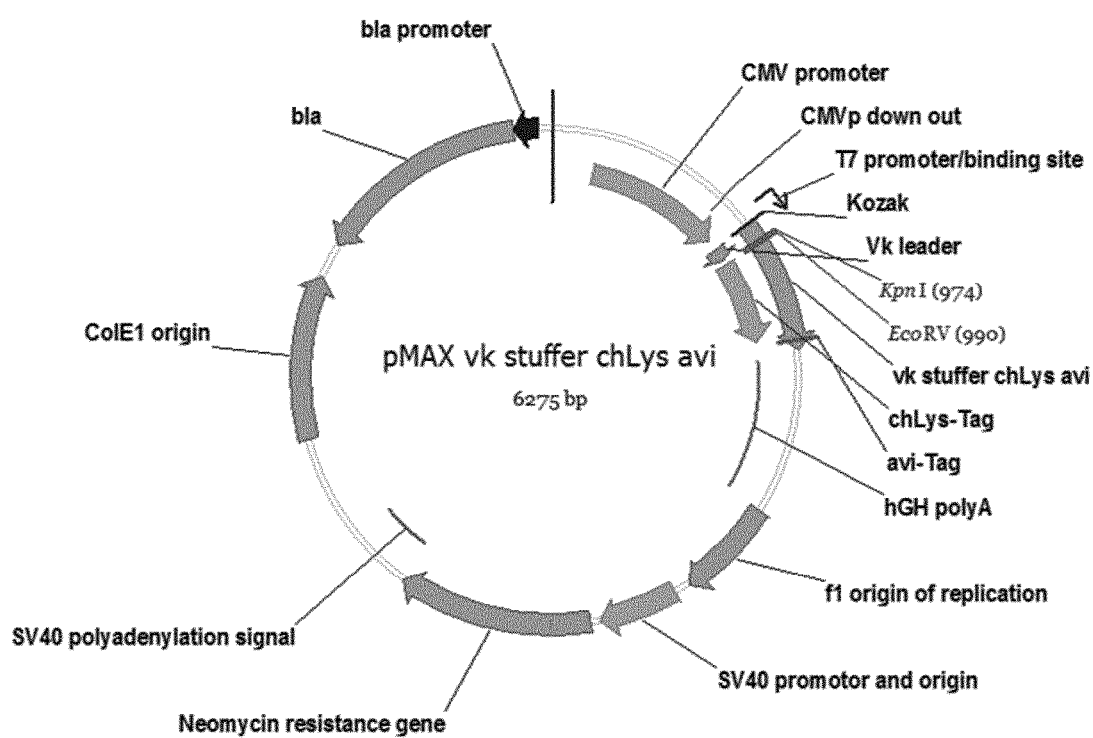
FIG. 1: Vector used for expression of lyzosyme fusion protein. Sequence encoding chicken lysozyme was subcloned into pMax vector backbone.

In one aspect the disclosure refers to a method for enhancing the expression of a polypeptide or protein of interest, by expressing said polypeptide or protein of interest as a fusion protein comprising lysozyme.

In one embodiment of the disclosure the polypeptide or protein of interest is a monomeric polypeptide or protein of interest. In a further embodiment the polypeptide or protein of interest has a physiological monomeric composition. In another embodiment the polypeptide or protein of interest has a physiological monomeric composition and acts as a monomer. In another embodiment the protein of interest is a cell surface receptor which is physiologically expressed as a monomer. In a further embodiment the protein of interest is a soluble protein which is physiologically expressed as a monomer.

In one embodiment of the disclosure the fusion protein comprises a polypeptide or protein of interest and lysozyme wherein lysozyme is fused to the N-terminus of the polypeptide or protein of interest. In one embodiment of the disclosure the fusion protein comprises a polypeptide or protein of interest and lysozyme wherein lysozyme is fused to the C-terminus of the polypeptide or protein of interest.

In one embodiment the disclosure refers to a method for enhancing the expression of a polypeptide or protein of interest, by expressing said polypeptide or protein of interest as a fusion protein comprising lysozyme, wherein the yield of said fusion protein is at least 2-fold higher than the yield compared to the polypeptide or protein of interest not comprising lysozyme.

In one embodiment the disclosure refers to a method for enhancing the expression of a polypeptide or protein of interest, by expressing said polypeptide or protein of interest as a fusion protein comprising lysozyme, wherein the fusion protein comprising the polypeptide or protein of interest and lysozyme does not form any aggregates or inclusion bodies. In a further embodiment of the disclosure less than 50%, 40%, 30%, 25%, 20%, 15%, 14%, 13%, 12%, 11%, 10%, 9%, 8%, 7%, 6%, 5%, 4%, 3%, 2%, 1% of the fusion protein comprising the polypeptide or protein of interest and lysozyme forms aggregates.

In one embodiment of the disclosure said fusion protein is expressed in a host cell. In a further embodiment of the disclosure said host cell is a prokaryotic cell or a eukaryotic cell. In a preferred embodiment the host cell is a eukaryotic cell. In a more preferred embodiment of the disclosure said eukaryotic cell is a selected from a CHO cell, a PER.C6 cell, a HKB11 cell and a HEK293 cell.

In one embodiment of the disclosure said host cell was transfected with an expression vector encoding said fusion protein comprising the polypeptide or protein of interest and lysozyme.

In one embodiment of the disclosure said fusion protein is expressed in a host cell wherein the cultivation of said host cell requires at least 50% less antibiotics as a supplement for the culture medium compared to culture medium for the cultivation of said protein or polypeptide of interest not fused to lysozyme. In a preferred embodiment of the disclosure said fusion protein is expressed in a host cell wherein the cultivation of said host cell requires at least 50% less, 60% less, 70% less, 80% less, 90% less, or 95% less antibiotics as a supplement for the culture medium compared to culture medium for the cultivation of said protein or polypeptide of interest not fused to lysozyme. In a more preferred embodiment of the disclosure said fusion protein is expressed in a host cell wherein the culture medium for the cultivation of said host cell is free of antibiotics.

In one embodiment of the disclosure said fusion protein comprising the polypeptide or protein of interest and lysozyme is isolated after expression. In a further embodiment of the disclosure said fusion protein is isolated from the host cell, the culture medium or both.

In one embodiment of the disclosure said fusion protein is isolated with an antibody specific for lysozyme. In a further embodiment of the disclosure the antibody specific for lysozyme is an isolated antibody. In a preferred embodiment of the disclosure the antibody specific for lysozyme is a monoclonal antibody. In a preferred embodiment of the disclosure the antibody specific for lysozyme comprises an HCDR1 region of sequence NSAAWS (SEQ ID NO: 9), an HCDR2 region of sequence RIYYRSKWYNDYAVSVKS (SEQ ID NO: 10), an HCDR3 region of sequence LDHRYHEDTVYPGMDV (SEQ ID NO: 11), an LCDR1 region of sequence SGDNLPAYTVT (SEQ ID NO: 12), an LCDR2 region of sequence DDSDRPS (SEQ ID NO: 13), and an LCDR3 region of sequence ASWDPSSGV (SEQ ID NO: 14). In a preferred embodiment of the disclosure the antibody specific for lysozyme is MOR03207. In another embodiment of the disclosure the antibody specific for lysozyme binds to the same epitope as MOR03207. In a further embodiment of the disclosure the antibody specific for lysozyme competes with MOR03207.

In one embodiment of the disclosure the antibody specific for lysozyme is attached to a support substrate. In further embodiments of the disclosure the antibody specific for lysozyme is attached to a support substrate selected from the group consisting of agarose, sepharose, polyacrylamide, agarose/polyacrylamide co-polymers, dextran, cellulose, polypropylene, polycarbonate, nitrocellulose, glass, paper and magnetic particles. In a further embodiment the support substrate is incorporated into a purification column. In a further embodiment the support substrate is incorporated on separable beads.

In one aspect of the disclosure the polypeptide or protein of interest is fused to a mammalian lysozyme. In one embodiment the mammalian lysozyme is selected from the group consisting of human, mouse, rat, chicken, rabbit, goat and primate lysozyme. In a preferred embodiment the mammalian lysozyme is chicken lysozyme.

In one aspect of the disclosure the polypeptide or protein of interest is fused to lysozyme or a fragment, analogue, homologue, variant or derivative thereof. In one embodiment the lysozyme or fragment, analogue, homologue, variant or derivative thereof is derived from mammalian lysozyme. In a further embodiment the mammalian lysozyme is selected from the group consisting of human, mouse, rat, chicken, rabbit, goat and primate lysozyme. In a preferred embodiment the mammalian lysozyme is chicken lysozyme.

In one embodiment the fusion protein comprises the polypeptide or protein of interest, lysozyme or a fragment, analogue, homologue, variant or derivative thereof and a protease cleavage site. In a preferred embodiment the cleavage site is FactorXa, Enterokinase (enteropeptidase), TEV-Protease or HRV3C-Protease (PreScission Protease). In a preferred embodiment the protease cleavage site can be used for removal of the lysozyme polypeptide domain.

In one aspect the present disclosure refers to a kit comprising an expression vector encoding a fusion protein which comprises a polypeptide or protein of interest and lysozyme and an antibody specific for lysozyme. In one embodiment said antibody specific for lysozyme is attached to a support substrate. In a preferred embodiment said support substrate is a solid support substrate. In a further embodiment said solid support substrate is selected from the group consisting of agarose, sepharose, polyacrylamide, agarose/polyacrylamide co-polymers, dextran, cellulose, polypropylene, polycarbonate, nitocellulose, glass, paper and magnetic particles.

In one aspect the present disclosure refers to a fusion protein comprising a polypeptide or protein of interest and lysozyme, wherein the polypeptide or protein of interest has a lengths of at least 5 amino acids, at least 10 amino acids, at least 20 amino acids, at least 50 amino acids, at least 80 amino acids, at least 90 amino acids, at least 100 amino acids, at least 110 amino acids, at least 120 amino acids, at least 125 amino acids, at least 150 amino acids, at least 200 amino acids, at least 250 amino acids, at least 300 amino acids, at least 400 amino acids or at least 500 amino acids.

In one aspect the present disclosure refers to a polypeptide or protein, which is tagged with lysozyme. In one embodiment the polypeptide or protein, which is tagged with lysozyme, is at least 5 amino acids, is at least 10 amino acids, is at least 20 amino acids, is at least 50 amino acids, is at least 80 amino acids, is at least 90 amino acids, is at least 100 amino acids, is at least 110 amino acids, is at least 120 amino acids, is at least 125 amino acids, is at least 150 amino acids, is at least 200 amino acids, is at least 250 amino acids, is at least 300 amino acids, is at least 400 amino acids or is at least 500 amino acids long.

In one aspect the disclosure refers to a method for enhancing the expression of a monomeric polypeptide or protein of interest, by expressing said monomeric polypeptide or protein of interest as a fusion protein comprising lysozyme.

In one embodiment the disclosure refers to a method for enhancing the expression of a monomeric polypeptide or protein of interest, by expressing said monomeric polypeptide or protein of interest as a fusion protein comprising lysozyme, wherein the yield of said fusion protein is at least 2-fold higher, at least 3-fold higher, at least 4-fold higher, at least 5-fold higher, at least 6-fold higher, at least 7-fold higher, at least 7-fold higher, at least 8-fold higher, at least 10-fold higher, at least 15-fold higher, at least 20-fold higher, at least 25-fold higher, at least 50-fold higher or at least 100-fold higher than the yield compared to the monomeric polypeptide or protein of interest not comprising lysozyme.

In one embodiment the disclosure refers to a method for enhancing the expression of a monomeric polypeptide or protein of interest, by expressing said monomeric polypeptide or protein of interest as a fusion protein comprising lysozyme, wherein the fusion protein comprising the monomeric polypeptide or protein of interest and lysozyme does not form any aggregates or inclusion bodies. In a further embodiment of the disclosure less than 50%, 40%, 30%, 25%, 20%, 15%, 14%, 13%, 12%, 11%, 10%, 9%, 8%, 7%, 6%, 5%, 4%, 3%, 2%, 1% of the fusion protein comprising the monomeric polypeptide or protein of interest and lysozyme forms aggregates.

In one embodiment of the disclosure said host cell was transfected with an expression vector encoding said fusion protein comprising the monomeric polypeptide or protein of interest and lysozyme.

In one embodiment of the disclosure the fusion protein comprises a monomeric polypeptide or protein of interest and lysozyme wherein lysozyme is fused to the N-terminus of the monomeric polypeptide or protein of interest. In one embodiment of the disclosure the fusion protein comprises a monomeric polypeptide or protein of interest and lysozyme wherein lysozyme is fused to the C-terminus of the monomeric polypeptide or protein of interest.

In one embodiment of the disclosure said fusion protein comprising the monomeric polypeptide or protein of interest and lysozyme is isolated after expression. In a further embodiment of the disclosure said fusion protein is isolated from the host cell, the culture medium or both.

In one aspect the disclosure refers to a method for the production of a fusion protein, said method comprising the steps of
(a) expressing said fusion protein in a host cell, and
(b) isolating said fusion protein,
wherein one of the polypeptide domains of said fusion protein is lysozyme.

In one embodiment of the disclosure the fusion protein is isolated from the host cell. In further embodiments the fusion protein is isolated from the culture medium. In a preferred embodiment the fusion protein is isolated from the host cell and the culture medium.

In one aspect the disclosure refers to a method for the production of a fusion protein, said method comprising the steps of
(a) expressing said fusion protein in a host cell, and
(b) isolating said fusion protein from the host cell and the culture medium,
wherein one of the polypeptide domains of said fusion protein is lysozyme and wherein the yield of said fusion protein in step (a) is at least 2-fold, 3-fold, 4-fold, 5-fold, 6-fold, 7-fold, 8-fold, 9-fold, 10-fold, 15-fold, 20-fold higher than the yield compared to a protein not comprising a lysozyme polypeptide domain.

In one aspect the disclosure refers to a method for the production of a fusion protein, said method comprising the steps of
(a) expressing said fusion protein in a host cell, and
(b) isolating said fusion protein from the host cell and the culture medium,
wherein one of the polypeptide domains of said fusion protein is lysozyme and wherein the fusion protein expressed in step (a) does not form any aggregates or inclusion bodies.

In one embodiment of the disclosure less than 50%, 40%, 30%, 25%, 20%, 15%, 14%, 13%, 12%, 11%, 10%, 9%, 8%, 7%, 6%, 5%, 4%, 3%, 2%, 1% of the isolated fusion protein form aggregates.

In one aspect the disclosure refers to a method for the production of an isolated polypeptide or protein of interest, said method comprising the steps of
(a) expressing a fusion protein in a host cell, wherein said fusion protein comprises said polypeptide or protein of interest and lysozyme and
(b) isolating said fusion protein.

In one embodiment of the disclosure the fusion protein is isolated from the host cell. In further embodiments the fusion protein is isolated from the culture medium. In a preferred embodiment the fusion protein is isolated from the host cell and the culture medium.

In one aspect the disclosure refers to a method for the production of an isolated monomeric polypeptide or protein.

In one aspect the disclosure refers to a method for the production of an isolated monomeric polypeptide or protein of interest. In a preferred embodiment the polypeptide or protein has a physiological monomeric composition. In a preferred embodiment the protein of interest has a physiological monomeric composition. In a preferred embodiment the protein of interest is a cell surface receptor which is physiologically expressed as a monomer. In a preferred embodiment the protein of interest is a soluble protein which is physiologically expressed as a monomer.

In one aspect the disclosure refers to a method for the production of an isolated monomeric polypeptide or protein of interest, said method comprising the steps of
(a) expressing a fusion protein in a host cell, wherein said fusion protein comprises said monomeric polypeptide or protein of interest and lysozyme and
(b) isolating said fusion protein from the host cell and the culture medium.

In one embodiment of the disclosure the yield of said fusion protein in step (a) is at least 2-fold, 3-fold, 4-fold, 5-fold, 6-fold, 7-fold, 8-fold, 9-fold, 10-fold, 15-fold, 20-fold higher than the yield compared to the monomeric polypeptide or protein of interest not comprising lysozyme.

In one embodiment of the disclosure the fusion protein expressed in step (a) does not form any aggregates or inclusion bodies. In a preferred embodiment of the disclosure less than 50%, 40%, 30%, 25%, 20%, 15%, 14%, 13%, 12%, 11%, 10%, 9%, 8%, 7%, 6%, 5%, 4%, 3%, 2%, 1% of the isolated fusion protein form aggregates.

In one embodiment of the disclosure lysozyme is a tag. In further embodiments lysozyme is an expression or purification tag. In a preferred embodiment lysozyme is an expression and purification tag.

In one aspect the disclosure refers to the use of lysozyme as a tag for the production of a polypeptide or protein of interest characterized by expressing a polypeptide or protein of interest fused to lysozyme and isolating said polypeptide or protein of interest fused to lysozyme.

In one aspect the disclosure refers to the use of lysozyme as a tag for the production of a polypeptide or protein of interest characterized by expressing a polypeptide or protein of interest fused to lysozyme in a host cell and isolating said polypeptide or protein of interest fused to lysozyme from the host cell and the culture medium.

In one aspect the disclosure refers to the use of lysozyme as a tag for the production of a polypeptide or protein of interest characterized by expressing a polypeptide or protein of interest fused to lysozyme in a host cell and isolating said polypeptide or protein of interest fused to lysozyme from the host cell and the culture medium wherein said polypeptide or protein of interest fused to lysozyme is isolated with an antibody specific for lysozyme.

In one embodiment of the disclosure the yield of said polypeptide or protein of interest fused to lysozyme is at least 2-fold, 3-fold, 4-fold, 5-fold, 6-fold, 7-fold, 8-fold, 9-fold, 10-fold, 15-fold, 20-fold higher than the yield compared said polypeptide or protein of interest not comprising a lysozyme polypeptide domain.

Definitions

The term "polypeptide" is used herein in its broadest sense as appreciated by the skilled artisan. Polypeptides comprise at least two amino acids linked via a peptide bond. Typically, polypeptides comprise more than 30 amino acids.

The term "protein" is also used herein in its broadest sense as appreciated by the skilled artisan. A protein comprises one or more polypeptides, where at least part of the polypeptide has or is able to acquire a defined three-dimensional structure arrangement by forming secondary, tertiary, or quaternary structures within and/or between its polypeptide chain(s). Proteins may be monomeric (composed of one polypeptide chain) or multimeric (composed of two or more polypeptide chains).

The term "host cell" as used herein may be any of a number commonly used cells in the production of exogenous polypeptides or proteins, including eukaryotic and prokaryotic host cells. Preferred host cells of the present invention are eukaryotic host cells, such as fungi cells, yeast cells, plant cells, insect cells or mammalian cells. Most preferred are mammalian host cells. In yet further preferred embodiments said mammalian host cell is selected from a CHO cell (European Collection of Cell Culture; ECACC #85050302), a PER.C6 cell (Crucell, Leiden, The Netherlands), a HKB11 cell (Bayer HealthCare, Berkley/CA, USA) and a HEK293 cell (American Type Culture Collection; Order no. CRL-1573).

The term "conditions that allow the expression [of a polypeptide]" as used herein refers to conditions that lead to the expression of a given polypeptide. The purposefully selection of the conditions of the host cell enables the switching on (or the shut down) of the expression of the polypeptides of the present invention. Typically such change of conditions is brought upon by the addition of a chemical or a naturally occurring compound, an "inducer", to the growth medium of the host cell. Depending on the specific promoter used the nature of the inducer varies. Other changes of conditions that may lead to the expression of polypeptides are an increase of temperature or an exposure to light or to UV.

The term "lysozyme" as used herein includes all naturally-occurring lysozymes, such as hen egg white lysozyme, synthetic lysozymes and recombinant lysozymes, such as human recombinant lysozyme, as well as lysozyme salts. In a preferred embodiment lysozyme is chicken lysozyme (SEQ ID NO: 1). In one embodiment the term "lysozyme" refers to lysozyme from microorganism such as algae, archea, bacteria, yeast, filamentous fungus, or protozoan. In one embodiment the term "lysozyme" refers to lysozyme from mammals, birds, reptile and amphibians. In one embodiment the term "lysozyme" refers to mouse (SEQ ID NO: 2), rabbit (SEQ ID NO: 3), goat (SEQ ID NO: 4), human (SEQ ID NO: 5), cow (SEQ ID NO: 6), rat (SEQ ID NO: 7) or cynomolgus (SEQ ID NO: 8) lysozyme. In a preferred embodiment the lysozyme used in the present disclosure shares at least 65%, at least 70%, at least 75%, at least 80%, at least 85%, at least 90%, at least 95%, at least 96%, at least 97%, at least 98% at least 99% or 100% identity in the amino acid sequence of the lysozyme which is expressed by a naturally occurring organism.

The term "variant" is defined herein as a polypeptide comprising an alteration, such as a substitution, insertion, and/or deletion, of one or more (several) amino acid residues at one or more (several) specific positions. The altered polypeptide (variant) may be obtained through human intervention by modification of the polynucleotide sequence encoding the parental lysozyme. The parental lysozyme may be encoded by SEQ ID NO: 1, 2, 3, 4, 5, 6, 7, 8 or a sequence which is at least 65%, at least 70%, at least 75%, at least 80%, at least 85%, at least 90%, at least 95%, at least 96%, at least 97%, at least 98% or at least 99% identical to one of these sequences. The variant polypeptide sequence is preferably one which is not found in nature. The present invention relates to lysozyme variants, comprising an alteration, preferably in the form of a substitution and/or an insertion and/or a deletion at one or more (several) positions.

The term "isolated" as used herein refers to a polypeptide or protein or variants thereof that is isolated from a source, e.g. the host cell from which it is expressed. Preferably, the polypeptide is at least 40% pure, such as, at least 60% pure, at least 80% pure, at least 90% pure or at least 95% pure, as determined by SDS-PAGE.

The term "fusion protein" refers to a single polypeptide chain having at least two polypeptide domains that are not normally present in a single, natural polypeptide. Thus, naturally occurring proteins are not "fusion proteins", as used herein. Preferably, a polypeptide of interest is fused with at least one polypeptide domain via a peptide bond and the fusion protein may also include the linking regions of amino acids between amino acid portions derived from separate proteins. The polypeptide domain fused to the polypeptide of interest may enhance solubility and/or expression of the polypeptide of interest and may also provide a purification tag to allow purification of the recombinant fusion protein from the host cell or culture supernatant, or both. The polypeptide domain fused to the polypeptide of interest may be fused at the N-terminus or at the C-terminus of the polypeptide of interest.

The term "recombinant" refers to an artificial combination of two otherwise separated segments of sequence, e.g., by chemical synthesis or by the manipulation of isolated segments of amino acids or of nucleic acids by genetic engineering techniques.

The term "expression", as used herein, refers to the production of a functional end-product e.g., a mRNA or a protein (precursor or mature).

The term "vector" is intended to refer to a polynucleotide molecule capable of transporting another polynucleotide to which it has been linked. One type of vector is a "plasmid", which refers to a circular double stranded DNA loop into which additional DNA segments may be inserted. Moreover, the coding sequence of the gene-of-interest can be transcribed from certain vectors by the cellular transcription machinery and further translated into the protein of interest. Such vectors are referred to herein as "expression vectors". In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "monomeric", and grammatical equivalents thereof, as used herein refer to a polypeptide or protein which consists of a single polypeptide chain. Monomeric polypeptides or proteins of the present invention are neither covalently nor non-covalently associated with or bound to another polypeptide or protein.

The term "tag" is used herein and refers to a peptide or polypeptide sequence that can be attached to a second polypeptide. Preferably, a tag is a purification tag or an expression tag, or both.

The term "purification tag" as used herein refers to any peptide sequence suitable for purification or identification of a polypeptide. The purification tag specifically binds to another moiety with affinity for the purification tag. Such moieties which specifically bind to a purification tag are usually attached to a matrix or a resin, such as agarose beads. Moieties which specifically bind to purification tags include antibodies, other proteins (e.g. Protein A or Streptavidin), nickel or cobalt ions or resins, biotin, amylose, maltose, and cyclodextrin. Exemplary purification tags include histidine (HIS) tags (such as a hexahistidine peptide), which will bind to metal ions such as nickel or cobalt ions. Other exemplary purification tags are the myc tag (EQKLISEEDL), the Strep tag (WSHPQFEK), the Flag tag (DYKDDDDK) and the V5 tag (GKPIPNPLLGLDST). The term "purification tag" also includes "epitope tags", i.e. peptide sequences which are specifically recognized by antibodies. Exemplary epitope tags include the FLAG tag, which is specifically recognized by a monoclonal anti-FLAG antibody. The peptide sequence recognized by the anti-FLAG antibody consists of the sequence DYKDDDDK or a substantially identical variant thereof. The term "purification tag" also includes substantially identical variants of purification tags. "Substantially identical variant" as used herein refers to derivatives or fragments of purification tags which are modified compared to the original purification tag (e.g. via amino acid substitutions, deletions or insertions), but which retain the property of the purification tag of specifically binding to a moiety which specifically recognizes the purification tag.

The term "expression tag" as used herein refers to any peptide or polypeptide that can be attached to a second polypeptide and is supposed to support the solubility, stability and/or the expression of a recombinant polypeptide of interest. Exemplary expression tags include Fc-tag and SUMO-tag. In principle, any peptide, polypeptide or protein can be used as an expression tag.

The term "antibody" as used herein includes whole antibodies and any fragment or single chains thereof. A naturally occurring "antibody" is a protein comprising at least two heavy (H) chains and two light (L) chains inter-connected by disulfide bonds. In a preferred embodiment the antibody disclosed in the application is a "monoclonal antibody". The term "monoclonal antibody" as used herein refers to a preparation of antibody molecules of single molecular composition. A monoclonal antibody composition displays a unique binding site having a unique binding specificity and affinity for particular epitopes.

The term "transfection" as used herein refers to a wide variety of techniques commonly used for the introduction of exogenous DNA into a prokaryotic or eukaryotic host cell, e.g., electroporation, calcium-phosphate precipitation, DEAE-dextran transfection and the like. The host cell may be "transfected" with the vector of the present invention by any conventional means known to the skilled artisan. For example transfection may be a transient transfection. Therefore in certain embodiments of the present invention said gene encoding said fusion protein comprising the polypeptide or protein of interest and lysozyme is introduced into said eukaryotic host cell via transient transfection.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

| Lysozyme SEQ #/Species | Sequence |
|---|---|
| SEQ ID NO: 1<br>Chicken<br>(*Gallus Gallus*) | KVFGRCELAAAMKRHGLDNYRGYSLGNWVCAAKFESNFNTQATNRN<br>TDGSTDYGILQINSRWWCNDGRTPGSRNLCNIPCSALLSSDITASVNC<br>AKKIVSDGNGMNAWVAWRNRCKGTDVQAWIRGCRL |
| SEQ ID NO: 2<br>Mouse<br>(*Mus Musculus*) | KVYNRCELARILKRNGMDGYRGVKLADWVCLAQHESNYNTRATNYN<br>RGDRSTDYGIFQINSRYWCNDGKTPRSKNACGINCSALLQDDITAAIQ<br>CAKRVVRDPQGIRAWVAWRTQCQNRDLSQYIRNCGV |
| SEQ ID NO: 3<br>Rabbit<br>(*Oryctolagus cuniculus*) | KIYERCELARTLKKLGLDGYKGVSLANWMCLTKWESSYNTQATNYNP<br>GDKSTDYGIFQINSRYWCNDGKTPRAVNACHIPCSDLLKDDITQAVAC<br>AKRVVSDPQGIRAWVAWRNHCQSQDLTSYIQGCGV |
| SEQ ID NO: 4<br>Goat<br>(*Capra hircus*) | KVFERCELARTLKRFGMDGFRGISLANWMCLARWESSYNTQATNYN<br>SGDRSTDYGIFQINSHWWCNDGKTPGAVNACHIPCSALLQDDITQAV<br>ACAKRVVSDPQGIRAWVAWRSHCQNQDLTSYIQGCGV |
| SEQ ID NO: 5<br>Human<br>(*Homo sapiens*) | KVFERCELARTLKRLGMDGYRGISLANWMCLAKWESGYNTRATNYN<br>AGDRSTDYGIFQINSRYWCNDGKTPGAVNACHLSCSALLQDNIADAV<br>ACAKRVVRDPQGIRAWVAWRNRCQNRDVRQYVQGCGV |
| SEQ ID NO: 6<br>Cow<br>(*Bos taurus*) | KVFERCELARTLKKLGLDGYKGVSLANWLCLTKWESSYNTKATNYNP<br>SSESTDYGIFQINSKWWCNDGKTPNAVDGCHVSCSELMENDIAKAVA<br>CAKHIVSEQGITAWVAWKSHCRDHDVSSYVQGCTL |

-continued

| Lysozyme SEQ #/Species | Sequence |
|---|---|
| SEQ ID NO: 7 Rat (Rattus norvegicus) | KIYERCEFARTLKRNGMSGYYGVSLADWVCLAQHESNYNTQARNYN PGDQSTDYGIFQINSRYWCNDGKTPRAKNACGIPCSALLQDDITQAIQ CAKRVVRDPQGIRAWVAWQRHCKNRDLSGYIRNCGV |
| SEQ ID NO: 8 Cynomolgus (Macaca fascicularis) | ASLISRCDLAQVLQLEDLDGFESYSLSDWLCLAFVESKFNISKINENAD GSFDYGLFQINGHYWCNDYRSHSENLCQVDCQGLARAPGWER |

EXAMPLES

All reagents are commercially available and purchased e.g. from Sigma-Aldrich, Sartorius, TTP, GE Healthcare, etc. and are standard reagents used in a molecular biology laboratory.

Unless indicated otherwise the molecular cloning was performed using standard protocols, essentially as described in Sambrook et al.: Molecular Cloning: A Laboratory Manual, 3 Vol.; Cold Spring Harbor Laboratory (December 2000). Expression and purification were performed according to standard procedures as described in Current Protocols in Protein Science (Wiley Interscience).

Example 1

Generation of a Vector Suitable for Use in the Methods of the Present Invention

Eukaryotic expression vectors, e.g. a standard pcDNA3.1 vector (Invitrogen) or a pMAX expression vector (FIG. 1, FIG. 2), which is a modified expression vector based on pcDNA3.1, were used to carry out the present invention. The pMAX expression vector e.g. comprises an origin of replication, antibiotic resistance as well as regulatory sequences (e.g. promotor, enhancer, polyadenylation site) for efficient transcription and translation. The respective fusion partners or tags (e.g. lysozyme, GST, His, Fc) were inserted at the 3'-end of the multiple cloning site (MCS) by standard sub-cloning (FIG. 1). In FIG. 2 the nucleotide sequence of the pMax expression construct comprising chicken lysozyme is exemplified.

The coding sequence of any protein of interest can be inserted into the MCS of the expression vector resulting in a fusion construct of the gene of interest and e.g. the lysozyme. The obtained vector was transfected into mammalian host cells, e.g. HKB11 or HEK293 cells, under conditions that the fusion protein comprising a protein-of-interest was expressed.

Example 2

Transfection of the Vector into Suitable Host Cells

Different variants of expression vectors according to Example 1 were generated encoding specific proteins of interest fused to a specific tag (e.g. lysozyme, GST, His, Fc) and were transfected into mammalian host cells.

For example, HKB11 suspension cells were seeded at a density of $0.5 \times 10^6$ vc/ml and incubated at 37° C. and 6% $CO_2$ in a humidified $CO_2$ incubator. The next day cells were transfected with plasmid-DNA using Lipofectamin2000 and OptiMEM (Invitrogen) according to the manufacturer's instructions. Three days later the conditioned cell culture supernatant was harvested. Afterwards, the expressed protein was purified from the harvested supernatant by standard purification methods (Protein A affinity chromatography for Fc-tag or IMAC for His-tag) or using an antibody specific for lysozyme (MOR03207) for lysozyme-tagged proteins. In this case the antibody specific for lysozyme was coupled to Sepharose 4 FF (GE Healthcare) according to the manufacturer's instructions. The expressed fusion protein of interest was bound to the column and the sample was eluted with 100 mM Glycin, pH 4.0.

Measurement of the UV absorbance at 280 nm was used for protein concentration determination. The native state of the purified protein was analyzed by size-exclusion-chromatography (used for determination of % aggregates) and dynamic light scattering (used for determination of particle size).

Example 3

Expression and Purification of Proteins of Interest Using Lysozyme as a Tag 3.1 Eight Proteins Analyzed Eight proteins of interest were selected for expression and purification as lysozyme fusion proteins. All proteins were expressed and secreted by mammalian cell lines (e.g. HKB11) and were purified from the cell culture supernatant. The selected proteins showed very low expression rates and/or high aggregation as Fc-, GST-fusions or as His-tagged proteins. In contrast, fusion with lysozyme leads to increased expression rates and/or highly improved protein quality throughout all examples.

In Tables 1-8 expression and purification of eight different proteins were tested and compared. All analyzed proteins of interest are proteins which are physiologically expressed as monomers and are longer than 110 amino acids. Exemplified proteins have a minimum size of 116 amino acids in the case protein 1, wherein protein 2 is 517 amino acids long, protein 3 is 257 amino acids long, protein 4 is 237 amino acids long, protein 5 is 217 amino acids long, protein 6 and protein 7 are both 193 amino acids long and protein 8 is 209 amino acids long.

Some exemplified proteins turned out to be not expressed when fused to the Fc-tag. Consequently, the His-tag, lysozyme or combinations thereof were tested to express said monomeric proteins of interest. Subsequent purification was either done via His-tag or via lysozyme. The Avi-tag was used oas a further tag for subsequent biotinylation of respective proteins. The Avi-tag is 15 amino acids long and comprises a recognition site for the BirA enzyme which mediates site-specific biotinylation. The Avi-tag has no impact on the expression level of a recombinantly expressed polypeptide or protein and does not impair its tendency to aggregate.

3.2 Lysozyme-Tag Enabled or Enhances Protein Expression

Protein 1 was encoded on a mammalian expression vector and was fused to specific combinations of two different tags. Thereby, either an His-tag or a lysozyme tag was used and the purification was done via the His-tag (using immobilized metal affinity chromatography, IMAC) or via lysozyme (using MOR3207 as a lysozyme specific antibody coupled to Sepharose 4 FF). While no expression of Protein 1 was detectable using the His-tag, the fusion with lysozyme enabled the expression of Protein 1 (Table 1). Additionally, the purification of the fusion protein via a lysozyme specific antibody yielded in significantly higher amounts in comparison to the purification via IMAC. Furthermore, no aggregation of the purified protein was detectable.

TABLE 1

Expression and purification of a protein 1 fused to a His- or a lysozyme-tag. Protein 1 has a size of 116 aa.

| Construct | Expression | Purification | Yield [mg/L] | Aggregates[2] [%] |
|---|---|---|---|---|
| pMAX_Protein 1_His | 200 ml transient | IMAC | 0 | n.d. |
| pMAX_Protein 1_Lys | 200 ml transient | Lys (MOR3207) | 2.0 | 0 |

In Tables 2 and 3 further proteins are exemplified which could not be expressed using a combination of Fc- or His-tag. However, the fusion with lysozyme enabled expression and purification of both proteins, Protein 2 and Protein 3. For Protein 2 an increase of yield after purification from 0.3 mg/L to 4.0 mg/L was achieved by fusing lysozyme to Protein 2. Furthermore the level of aggregations was below 7% of the purified fusion proteins.

TABLE 2

Expression and purification of protein 2 fused to a Fc-, His- or lysozyme-tag. Protein 2 has a size of 517 aa.

| Construct | Expression | Purification | Yield [mg/L] | Aggregates [%] |
|---|---|---|---|---|
| pMAX_Protein 2_Fc-Avi_His | 600 ml transient | IMAC | 0.3 | n.d. |
| pMAX_Protein 2 Avi-His | 600 ml transient | IMAC | 0 | n.d. |
| pMAX_Protein 2_Lys-Avi | 200 ml transient | Lys (MOR3207) | 4.0 | 3.44% |

TABLE 3

Expression and purification of protein 3 fused to a Fc-, His- or lysozyme-tag. Protein 3 has a size of 257 aa.

| Construct | Expression | Purification | Yield [mg/L] | Aggregates [%] |
|---|---|---|---|---|
| pMAX_Protein 3_Fc_His | 200 ml transient | IMAC | 0 | n.d. |
| pMAX_Protein 3_His | 200 ml transient | IMAC | 0 | n.d. |
| pMAX_Protein 3-Lys-His | 200 ml transient | Lys (MOR3207) | 0.4 | 6.6 |
| pMAX_Protein 3_Lys-Avi | 200 ml transient | Lys (MOR3207) | 0.1 | 2 |

3.2 Lysozyme Fusion Proteins Show Less Aggregation

Analyzed proteins 4, 5 and 6 not only showed enhanced expression rates but also less aggregation if expressed as lysozyme-fusion protein. Expression of protein 4 was increased more than 3-fold and aggregation was reduced more than 3-fold if protein was tagged with lysozyme instead of His (Table 4).

TABLE 4

Expression and purification of a specific protein fused to the His- or the lysozyme-tag. Protein 4 has a size of 237 aa.

| Construct | Expression | Purification | Yield [mg/L] | Aggregates [%] |
|---|---|---|---|---|
| pMAX_Protein 4_His | 200 ml transient | IMAC | 3.4 | 7 |
| pMAX_Protein 4_Lys-Avi | 200 ml transient | Lys (MOR3207) | 13 | 2 |

Similar results were observed with proteins 5 (Table 5) and 6 (Table 6) when the lysozyme tag was compared to the GST-tag.

TABLE 5

Expression and purification of a specific protein fused to the GST- or to the lysozyme-tag. Protein 5 has a size of 217 aa.

| Construct | Expression | Purification | Yield [mg/L] | Aggregates [%] |
|---|---|---|---|---|
| pMAX_Protein 5_GST_His | 200 ml transient | IMAC | 3.8 | 13.4 |
| pMAX_Protein 5_Lys-Avi | 200 ml transient | Lys (MOR3207) | 10.4 | 5.7 |

TABLE 6

Expression and purification of a specific protein fused to a GST- or lysozyme-tag. Protein 6 has a size of 193 aa.

| Construct | Expression | Purification | Yield [mg/L] | Aggregates [%] |
|---|---|---|---|---|
| pMAX_Protein 6_GST_His | 200 ml transient | IMAC | 8.8 | 10 |
| pMAX_Protein 6_Lys-Avi | 200 ml transient | Lys (MOR3207) | 13.5 | <2 |

Accordingly, proteins analyzed in Tables 7 and 8 could also be purified with significantly lower aggregation upon tagging with lysozyme in comparison to the proteins fused to a GST-His or His-tag. Additionally, expression levels of protein 8 were increased by lysozyme-fusion in comparison to the GST-His- or His-tag, while expression levels of protein 7 were only increased in comparison to the His-tag but not to the GST-His-tag.

TABLE 7

Expression and purification of a specific protein fused to a GST-, His- or lysozyme-tag. Protein 7 has a size of 193 aa.

| Construct | Expression | Purification | Yield [mg/L] | Aggregates [%] |
|---|---|---|---|---|
| pMAX_Protein 7_GST_His | 200 ml transient | IMAC | 19.2 | 17 |
| pMAX_Protein 7_His | 200 ml transient | IMAC | 4.2 | 5 (two species) |
| pMAX_Protein 7_Lys-Avi | 200 ml transient | Lys (MOR3207) | 9.8 | 5 |

TABLE 8

Expression and purification of a specific protein fused a GST-, His- or lysozyme-tag. Protein 8 has a size of 209 aa.

| Construct | Expression | Purification | Yield [mg/L] | Aggregates [%] |
|---|---|---|---|---|
| pMAX_Protein 8_GST_His | 200 ml transient | IMAC | 4.7 | 17 |
| pMAX_Protein 8_His | 200 ml transient | IMAC | 1.2 | Low recovery in SEC due to aggregates |
| pMAX_Protein 8_Lys-Avi | 200 ml transient | Lys (MOR3207) | 7.5 | 0 |

3.3 Summary

Taken together, the fusion of lysozyme to all proteins analyzed was advantageous in comparison to alternative tags (e.g. His, GST_His, Fc_His, His).

For proteins 1, 2 and 3 the expression levels were significantly increased when proteins were fused to lysozyme. For protein 7, expression levels were not increased but fusion to lysozyme significantly improved the quality of the purified protein in terms of reduced aggregation. However, for the proteins 4, 5, 6 and 8 we observed a significantly reduced tendency to aggregate accompanied with an increased expression rate when proteins were fused to lysozyme.

The invention claimed is:

1. A method for the production of an isolated monomeric polypeptide or protein, said method comprising the steps of
   (a) expressing said monomeric polypeptide or protein as a fusion protein in a host cell, wherein said fusion protein comprises said monomeric polypeptide or protein and lysozyme, and wherein said fusion protein is secreted from the host cell into cell culture supernatant; and
   (b) isolating said secreted fusion protein from the cell culture supernatant.

2. The method according to claim 1, wherein the yield of said fusion protein is at least 2-fold higher than the yield compared to the monomeric polypeptide or protein not comprising lysozyme.

3. The method according to claim 1, wherein less than 15% of the fusion protein comprising the monomeric polypeptide or protein and lysozyme forms aggregates.

4. The method according to claim 1, wherein said host cell is a prokaryotic cell or a eukaryotic cell.

5. The method according to claim 1, wherein said host cell was transfected with an expression vector encoding said fusion protein comprising the monomeric polypeptide or protein, and lysozyme.

6. The method according to claim 1, wherein said monomeric polypeptide or protein has a length of at least 100 amino acids.

7. The method according to claim 1, wherein said fusion protein is isolated with an antibody specific for lysozyme.

8. The method according to claim 1, wherein said lysozyme is a mammalian lysozyme.

9. The method according to claim 1, wherein said lysozyme is a fragment, analogue, homologue, variant or derivative of lysozyme.

* * * * *

SEQUENCE LISTING

```
<160> NUMBER OF SEQ ID NOS: 15

<210> SEQ ID NO 1
<211> LENGTH: 129
<212> TYPE: PRT
<213> ORGANISM: Gallus gallus
<220> FEATURE:
<221> NAME/KEY: SOURCE
<222> LOCATION: 1..129
<223> OTHER INFORMATION: /mol_type="protein"
      /note="Chicken lysozyme"
      /organism="Gallus gallus"

<400> SEQUENCE: 1

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
                20                  25                  30

Lys Phe Glu Ser Asn Phe Asn Thr Gln Ala Thr Asn Arg Asn Thr Asp
            35                  40                  45

Gly Ser Thr Asp Tyr Gly Ile Leu Gln Ile Asn Ser Arg Trp Trp Cys
        50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 2
<211> LENGTH: 130
<212> TYPE: PRT
<213> ORGANISM: Mus musculus
<220> FEATURE:
<221> NAME/KEY: SOURCE
<222> LOCATION: 1..130
```

```
<223> OTHER INFORMATION: /mol_type="protein"
     /note="Mouse lysozyme"
     /organism="Mus musculus"

<400> SEQUENCE: 2
```

Lys Val Tyr Asn Arg Cys Glu Leu Ala Arg Ile Leu Lys Arg Asn Gly
1               5                   10                  15

Met Asp Gly Tyr Arg Gly Val Lys Leu Ala Asp Trp Val Cys Leu Ala
            20                  25                  30

Gln His Glu Ser Asn Tyr Asn Thr Arg Ala Thr Asn Tyr Asn Arg Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Arg Ser Lys Asn Ala Cys Gly Ile Asn
65                  70                  75                  80

Cys Ser Ala Leu Leu Gln Asp Asp Ile Thr Ala Ala Ile Gln Cys Ala
                85                  90                  95

Lys Arg Val Val Arg Asp Pro Gln Gly Ile Arg Ala Trp Val Ala Trp
            100                 105                 110

Arg Thr Gln Cys Gln Asn Arg Asp Leu Ser Gln Tyr Ile Arg Asn Cys
        115                 120                 125

Gly Val
    130

```
<210> SEQ ID NO 3
<211> LENGTH: 130
<212> TYPE: PRT
<213> ORGANISM: Oryctolagus cuniculus
<220> FEATURE:
<221> NAME/KEY: SOURCE
<222> LOCATION: 1..130
<223> OTHER INFORMATION: /mol_type="protein"
     /note="Rabbit lysozyme"
     /organism="Oryctolagus cuniculus"

<400> SEQUENCE: 3
```

Lys Ile Tyr Glu Arg Cys Glu Leu Ala Arg Thr Leu Lys Lys Leu Gly
1               5                   10                  15

Leu Asp Gly Tyr Lys Gly Val Ser Leu Ala Asn Trp Met Cys Leu Thr
            20                  25                  30

Lys Trp Glu Ser Ser Tyr Asn Thr Gln Ala Thr Asn Tyr Asn Pro Gly
        35                  40                  45

Asp Lys Ser Thr Asp Tyr Gly Ile Phe Gln Ile Asn Ser Arg Tyr Trp
    50                  55                  60

Cys Asn Asp Gly Lys Thr Pro Arg Ala Val Asn Ala Cys His Ile Pro
65                  70                  75                  80

Cys Ser Asp Leu Leu Lys Asp Ile Thr Gln Ala Val Ala Cys Ala
                85                  90                  95

Lys Arg Val Val Ser Asp Pro Gln Gly Ile Arg Ala Trp Val Ala Trp
            100                 105                 110

Arg Asn His Cys Gln Ser Gln Asp Leu Thr Ser Tyr Ile Gln Gly Cys
        115                 120                 125

Gly Val
    130

```
<210> SEQ ID NO 4
<211> LENGTH: 130
<212> TYPE: PRT
<213> ORGANISM: Capra hircus
```

```
<220> FEATURE:
<221> NAME/KEY: SOURCE
<222> LOCATION: 1..130
<223> OTHER INFORMATION: /mol_type="protein"
      /note="Goat lysozyme"
      /organism="Capra hircus"

<400> SEQUENCE: 4

Lys Val Phe Glu Arg Cys Glu Leu Ala Arg Thr Leu Lys Arg Phe Gly
1               5                   10                  15

Met Asp Gly Phe Arg Gly Ile Ser Leu Ala Asn Trp Met Cys Leu Ala
            20                  25                  30

Arg Trp Glu Ser Ser Tyr Asn Thr Gln Ala Thr Asn Tyr Asn Ser Gly
        35                  40                  45

Asp Arg Ser Thr Asp Tyr Gly Ile Phe Gln Ile Asn Ser His Trp Trp
    50                  55                  60

Cys Asn Asp Gly Lys Thr Pro Gly Ala Val Asn Ala Cys His Ile Pro
65                  70                  75                  80

Cys Ser Ala Leu Leu Gln Asp Asp Ile Thr Gln Ala Val Ala Cys Ala
                85                  90                  95

Lys Arg Val Val Ser Asp Pro Gln Gly Ile Arg Ala Trp Val Ala Trp
            100                 105                 110

Arg Ser His Cys Gln Asn Gln Asp Leu Thr Ser Tyr Ile Gln Gly Cys
        115                 120                 125

Gly Val
    130

<210> SEQ ID NO 5
<211> LENGTH: 130
<212> TYPE: PRT
<213> ORGANISM: Homo sapiens
<220> FEATURE:
<221> NAME/KEY: SOURCE
<222> LOCATION: 1..130
<223> OTHER INFORMATION: /mol_type="protein"
      /note="Human lysozyme"
      /organism="Homo sapiens"

<400> SEQUENCE: 5

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130

<210> SEQ ID NO 6
```

```
<211> LENGTH: 129
<212> TYPE: PRT
<213> ORGANISM: Bos taurus
<220> FEATURE:
<221> NAME/KEY: SOURCE
<222> LOCATION: 1..129
<223> OTHER INFORMATION: /mol_type="protein"
      /note="Cow lysozyme"
      /organism="Bos taurus"

<400> SEQUENCE: 6
```

Lys Val Phe Glu Arg Cys Glu Leu Ala Arg Thr Leu Lys Lys Leu Gly
1               5                   10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Ser
        35                  40                  45

Ser Glu Ser Thr Asp Tyr Gly Ile Phe Gln Ile Asn Ser Lys Trp Trp
    50                  55                  60

Cys Asn Asp Gly Lys Thr Pro Asn Ala Val Asp Gly Cys His Val Ser
65                  70                  75                  80

Cys Ser Glu Leu Met Glu Asn Asp Ile Ala Lys Ala Val Ala Cys Ala
                85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Gln Gly Cys Thr
        115                 120                 125

Leu

```
<210> SEQ ID NO 7
<211> LENGTH: 130
<212> TYPE: PRT
<213> ORGANISM: Rattus norvegicus
<220> FEATURE:
<221> NAME/KEY: SOURCE
<222> LOCATION: 1..130
<223> OTHER INFORMATION: /mol_type="protein"
      /note="Rat lysozyme"
      /organism="Rattus norvegicus"

<400> SEQUENCE: 7
```

Lys Ile Tyr Glu Arg Cys Glu Phe Ala Arg Thr Leu Lys Arg Asn Gly
1               5                   10                  15

Met Ser Gly Tyr Tyr Gly Val Ser Leu Ala Asp Trp Val Cys Leu Ala
            20                  25                  30

Gln His Glu Ser Asn Tyr Asn Thr Gln Ala Arg Asn Tyr Asn Pro Gly
        35                  40                  45

Asp Gln Ser Thr Asp Tyr Gly Ile Phe Gln Ile Asn Ser Arg Tyr Trp
    50                  55                  60

Cys Asn Asp Gly Lys Thr Pro Arg Ala Lys Asn Ala Cys Gly Ile Pro
65                  70                  75                  80

Cys Ser Ala Leu Leu Gln Asp Asp Ile Thr Gln Ala Ile Gln Cys Ala
                85                  90                  95

Lys Arg Val Val Arg Asp Pro Gln Gly Ile Arg Ala Trp Val Ala Trp
            100                 105                 110

Gln Arg His Cys Lys Asn Arg Asp Leu Ser Gly Tyr Ile Arg Asn Cys
        115                 120                 125

Gly Val
    130

<210> SEQ ID NO 8
<211> LENGTH: 91
<212> TYPE: PRT
<213> ORGANISM: Macaca fascicularis
<220> FEATURE:
<221> NAME/KEY: SOURCE
<222> LOCATION: 1..91
<223> OTHER INFORMATION: /mol_type="protein"
    /note="Cynomolgus lysozyme"
    /organism="Macaca fascicularis"

<400> SEQUENCE: 8

Ala Ser Leu Ile Ser Arg Cys Asp Leu Ala Gln Val Leu Gln Leu Glu
1               5                   10                  15

Asp Leu Asp Gly Phe Glu Ser Tyr Ser Leu Ser Asp Trp Leu Cys Leu
            20                  25                  30

Ala Phe Val Glu Ser Lys Phe Asn Ile Ser Lys Ile Asn Glu Asn Ala
        35                  40                  45

Asp Gly Ser Phe Asp Tyr Gly Leu Phe Gln Ile Asn Gly His Tyr Trp
    50                  55                  60

Cys Asn Asp Tyr Arg Ser His Ser Glu Asn Leu Cys Gln Val Asp Cys
65                  70                  75                  80

Gln Gly Leu Ala Arg Ala Pro Gly Trp Glu Arg
                85                  90

<210> SEQ ID NO 9
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
    /note="MOR3207 HCDR1"
    /organism="Artificial Sequence"

<400> SEQUENCE: 9

Asn Ser Ala Ala Trp Ser
1               5

<210> SEQ ID NO 10
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
    /note="MOR3207 HCDR2"
    /organism="Artificial Sequence"

<400> SEQUENCE: 10

Arg Ile Tyr Tyr Arg Ser Lys Trp Tyr Asn Asp Tyr Ala Val Ser Val
1               5                   10                  15

Lys Ser

<210> SEQ ID NO 11
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
    /note="MOR3207 HCDR3"
    /organism="Artificial Sequence"

<400> SEQUENCE: 11

Leu Asp His Arg Tyr His Glu Asp Thr Val Tyr Pro Gly Met Asp Val
1               5                   10                  15

<210> SEQ ID NO 12
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="MOR3207 LCDR1"
      /organism="Artificial Sequence"

<400> SEQUENCE: 12

Ser Gly Asp Asn Leu Pro Ala Tyr Thr Val Thr
1               5                   10

<210> SEQ ID NO 13
<211> LENGTH: 7
<212> TYPE: PRT
<213> ORGANISM: Artificial Sequence
<220> FEATURE:
<221> NAME/KEY: SOURCE
<222> LOCATION: 1..7
<223> OTHER INFORMATION: /mol_type="protein"
      /note="MOR3207 LCDR2"
      /organism="Artificial Sequence"

<400> SEQUENCE: 13

Asp Asp Ser Asp Arg Pro Ser
1               5

<210> SEQ ID NO 14
<211> LENGTH: 9
<212> TYPE: PRT
<213> ORGANISM: Artificial Sequence
<220> FEATURE:
<221> NAME/KEY: SOURCE
<222> LOCATION: 1..9
<223> OTHER INFORMATION: /mol_type="protein"
      /note="MOR3207 LCDR3"
      /organism="Artificial Sequence"

<400> SEQUENCE: 14

Ala Ser Trp Asp Pro Ser Ser Gly Val
1               5

<210> SEQ ID NO 15
<211> LENGTH: 6275
<212> TYPE: DNA
<213> ORGANISM: Artificial Sequence
<220> FEATURE:
<221> NAME/KEY: source
<222> LOCATION: 1..6275
<223> OTHER INFORMATION: /mol_type="DNA"
      /note="pMAX"
      /organism="Artificial Sequence"

<400> SEQUENCE: 15
gatctcccga tcccctatgg tgcactctca gtacaatctg ctctgatgcc gcatagttaa     60
gccagtatct gctccctgct tgtgtgttgg aggtcgctga gtagtgcgcg agcaaaattt    120
aagctacaac aaggcaaggc ttgaccgaca tttgcatgaa gaatctgctt agggttaggc    180
gttttgcgct gcttcgcgat gtacgggcca gatatacgcg ttgacattga ttattgacta    240

```
gttattaata gtaatcaatt acggggtcat tagttcatag cccatatatg gagttccgcg    300
ttacataact tacggtaaat ggcccgcctg gctgaccgcc caacgacccc cgcccattga    360
cgtcaataat gacgtatgtt cccatagtaa cgccaatagg gactttccat tgacgtcaat    420
gggtggagta tttacggtaa actgcccact tggcagtaca tcaagtgtat catatgccaa    480
gtacgccccc tattgacgtc aatgacggta aatggcccgc ctggcattat gcccagtaca    540
tgaccttatg ggactttcct acttggcagt acatctacgt attagtcatc gctattacca    600
tggtgatgcg gttttggcag tacatcaatg ggcgtggata gcggtttgac tcacggggat    660
ttccaagtct ccaccccatt gacgtcaatg ggagtttgtt ttggcaccaa aatcaacggg    720
actttccaaa atgtcgtaac aactccgccc cattgacgca aatgggcggt aggcgtgtac    780
ggtgggaggt ctatataagc agagctctct ggctaactag agaacccact gcttactggc    840
ttatcgaaat taatacgact cactataggg agacccaagc tggctagcaa gcttctagcg    900
ccaccatggt gttgcagacc caggtcttca tttctctgtt gctctggatc tctggtgcct    960
acggggatgg taccgggaaa atgatggata tcatcgaggg ccggatggac aaggtgttcg   1020
gcagatgcga gctggccgct gccatgaagc ggcacggcct ggacaactac cggggctaca   1080
gcctgggcaa ctgggtctgc gccgccaagt tcgagagcaa cttcaatact caggccacca   1140
accggaacac cgacggcagc accgactacg gcatcctgca gatcaacagc cggtggtggt   1200
gcaacgacgg caggaccccc ggcagccgga acctgtgcaa catcccttgc agcgccctgc   1260
tgtccagcga catcaccgcc agcgtgaact gcgccaagaa aatcgtgtcc gacggcaacg   1320
gcatgaacgc ctgggtggcc tggcggaacc ggtgcaaggg cacagacgtg caggcctgga   1380
tcagaggctg cagactggtt aactctagag gtctgaacga catcttcgag gctcagaaaa   1440
tcgaatggca cgaataatga gaattctcta gataatgagt ttaaacgggt ggcatccctg   1500
tgacccctcc ccagtgcctc tcctggccct ggaagttgcc actccagtgc ccaccagcct   1560
tgtcctaata aaattaagtt gcatcatttt gtctgactag gtgtccttct ataatattat   1620
ggggtggagg ggggtggtat ggagcaaggg gcaagttggg aagacaacct gtagggcctg   1680
cggggtctat tgggaaccaa gctggagtgc agtggcacaa tcttggctca ctgcaatctc   1740
cgcctcctgg gttcaagcga ttctcctgcc tcagcctccc gagttgttgg gattccaggc   1800
atgcatgacc aggctcacct aatttttgtt tttttggtag agacggggtt tcaccatatt   1860
ggccaggctg gtctccaact cctaatctca ggtgatctac ccaccttggc ctcccaaatt   1920
gctgggatta caggcgtgaa ccactgctcc cttccctgtc cttctgattt taaaataact   1980
ataccagcag gaggacgtcc agacacagca taggctacct ggccatgccc aaccggtggg   2040
acatttgagt tgcttgcttg gcactgtcct ctcatgcgtt gggtccactc agtagatgcc   2100
tgttgaattg ggtacgcggc atcgattcca cgcgccctgt agcggcgcat taagcgcggc   2160
gggtgtggtg gttacgcgca gcgtgaccgc tacacttgcc agcgccctag cgcccgctcc   2220
tttcgctttc ttcccttcct ttctcgccac gttcgccggc tttccccgtc aagctctaaa   2280
tcggggggctc cctttagggt tccgatttag tgctttacgg cacctcgacc ccaaaaaact   2340
tgattagggt gatggttcac gtagtgggcc atcgccctga tagacggttt ttcgcccttt   2400
gacgttggag tccacgttct ttaatagtgg actcttgttc caaactggaa caacactcaa   2460
ccctatctcg gtctattctt ttgatttata gggattttg ccgatttcgg cctattggtt   2520
aaaaaatgag ctgatttaac aaaaatttaa cgcgaattaa ttctgtggaa tgtgtgtcag   2580
ttagggtgtg gaaagtcccc aggctcccca gcaggcagaa gtatgcaaag catgcatctc   2640
```

```
aattagtcag caaccaggtg tggaaagtcc ccaggctccc cagcaggcag aagtatgcaa    2700
agcatgcatc tcaattagtc agcaaccata gtcccgcccc taactccgcc catcccgccc    2760
ctaactccgc ccagttccgc ccattctccg ccccatggct gactaatttt ttttatttat    2820
gcagaggccg aggccgcctc tgcctctgag ctattccaga agtagtgagg aggcttttt    2880 ggaggcctag gcttttgcaa aaagctcccg ggagcttgta tatccatttt cggatctgat    2940
caagagacag gatgaggatc gtttcgcatg attgaacaag atggattgca cgcaggttct    3000
ccggccgctt gggtggagag gctattcggc tatgactggg cacaacagac aatcggctgc    3060
tctgatgccg ccgtgttccg gctgtcagcg caggggcgcc cggttctttt tgtcaagacc    3120
gacctgtccg gtgccctgaa tgaactgcag gacgaggcag cgcggctatc gtggctggcc    3180
acgacgggcg ttccttgcgc agctgtgctc gacgttgtca ctgaagcggg aagggactgg    3240
ctgctattgg gcgaagtgcc ggggcaggat ctcctgtcat ctcaccttgc tcctgccgag    3300
aaagtatcca tcatggctga tgcaatgcgg cggctgcata cgcttgatcc ggctacctgc    3360
ccattcgacc accaagcgaa acatcgcatc gagcgagcac gtactcggat ggaagccggt    3420
cttgtcgatc aggatgatct ggacgaagag catcaggggc tcgcgccagc cgaactgttc    3480
gccaggctca aggcgcgcat gcccgacggc gaggatctcg tcgtgaccca tggcgatgcc    3540
tgcttgccga atatcatggt ggaaaatggc cgcttttctg gattcatcga ctgtggccgg    3600
ctgggtgtgg cggaccgcta tcaggacata gcgttggcta cccgtgatat tgctgaagag    3660
cttggcggcg aatgggctga ccgcttcctc gtgctttacg gtatcgccgc tcccgattcg    3720
cagcgcatcg ccttctatcg ccttcttgac gagttcttct gagcgggact ctggggttcg    3780
aaatgaccga ccaagcgacg cccaacctgc catcacgaga tttcgattcc accgccgcct    3840
tctatgaaag gttgggcttc ggaatcgttt tccgggacgc cggctggatg atcctccagc    3900
gcggggatct catgctggag ttcttcgccc accccaactt gtttattgca gcttataatg    3960
gttacaaata aagcaatagc atcacaaatt tcacaaataa agcatttttt tcactgcatt    4020
ctagttgtgg tttgtccaaa ctcatcaatg tatcttatca tgtctgtata ccgtcgacct    4080
ctagctagag cttggcgtaa tcatggtcat agctgtttcc tgtgtgaaat tgttatccgc    4140
tcacaattcc acacaacata cgagccggaa gcataaagtg taaagcctgg ggtgcctaat    4200
gagtgagcta actcacatta attgcgttgc gctcactgcc cgctttccag tcgggaaacc    4260
tgtcgtgcca gctgcattaa tgaatcggcc aacgcgcggg gagaggcggt ttgcgtattg    4320
ggcgctcttc cgcttcctcg ctcactgact cgctgcgctc ggtcgttcgg ctgcggcgag    4380
cggtatcagc tcactcaaag gcggtaatac ggttatccac agaatcaggg gataacgcag    4440
gaaagaacat gtgagcaaaa ggccagcaaa aggccaggaa ccgtaaaaag gccgcgttgc    4500
tggcgttttt ccataggctc cgcccccctg acgagcatca caaaaatcga cgctcaagtc    4560
agaggtggcg aaacccgaca ggactataaa gataccaggc gtttccccct ggaagctccc    4620
tcgtgcgctc tcctgttccg accctgccgc ttaccggata cctgtccgcc tttctccctt    4680
cgggaagcgt ggcgctttct catagctcac gctgtaggta tctcagttcg gtgtaggtcg    4740
ttcgctccaa gctgggctgt gtgcacgaac cccccgttca gcccgaccgc tgcgccttat    4800
ccggtaacta tcgtcttgag tccaacccgg taagacacga cttatcgcca ctggcagcag    4860
ccactggtaa caggattagc agagcgaggt atgtaggcgg tgctacagag ttcttgaagt    4920
ggtggcctaa ctacggctac actagaagaa cagtatttgg tatctgcgct ctgctgaagc    4980
```

```
cagttacctt cggaaaaaga gttggtagct cttgatccgg caaacaaacc accgctggta      5040
gcggtggttt ttttgtttgc aagcagcaga ttacgcgcag aaaaaaagga tctcaagaag      5100
atcctttgat cttttctacg gggtctgacg ctcagtggaa cgaaaactca cgttaaggga      5160
ttttggtcat gagattatca aaaggatctc acctagat cctttaaat taaaaatgaa         5220 gttttaaatc aatctaaagt atatatgagt aaacttggtc tgacagttac caatgcttaa     5280
tcagtgaggc acctatctca gcgatctgtc tatttcgttc atccatagtt gcctgactcc     5340
ccgtcgtgta gataactacg atacgggagg gcttaccatc tggccccagt gctgcaatga     5400
taccgcgaga cccacgctca ccggctccag atttatcagc aataaaccag ccagccggaa     5460
gggccgagcg cagaagtggt cctgcaactt tatccgcctc catccagtct attaattgtt     5520
gccgggaagc tagagtaagt agttcgccag ttaatagttt gcgcaacgtt gttgccattg     5580
ctacaggcat cgtggtgtca cgctcgtcgt ttggtatggc ttcattcagc tccggttccc     5640
aacgatcaag gcgagttaca tgatccccca tgttgtgcaa aaaagcggtt agctccttcg     5700
gtcctccgat cgttgtcaga agtaagttgg ccgcagtgtt atcactcatg gttatggcag     5760
cactgcataa ttctcttact gtcatgccat ccgtaagatg cttttctgtg actggtgagt     5820
actcaaccaa gtcattctga gaatagtgta tgcggcgacc gagttgctct tgcccggcgt     5880
caatacggga taataccgcg ccacatagca gaactttaaa agtgctcatc attggaaaac     5940
gttcttcggg gcgaaaactc tcaaggatct taccgctgtt gagatccagt tcgatgtaac     6000
ccactcgtgc acccaactga tcttcagcat cttttacttt caccagcgtt tctgggtgag     6060
caaaaacagg aaggcaaaat gccgcaaaaa agggaataag ggcgacacgg aaatgttgaa     6120
tactcatact cttcctttt caatattatt gaagcattta tcagggttat tgtctcatga      6180
gcggatacat atttgaatgt atttagaaaa ataaacaaat aggggttccg cgcacatttc     6240
cccgaaaagt gccacctgac gtcgacggat cggga                                6275
```